United States Patent [19]

Wiersma

[11] Patent Number: 5,882,916
[45] Date of Patent: Mar. 16, 1999

[54] DECONTAMINATION PROCESS

[75] Inventor: Jack G. Wiersma, Jupiter, Fla.

[73] Assignee: Nouveau Technolgies, Inc., Fla.

[21] Appl. No.: 602,232

[22] Filed: Feb. 15, 1996

[51] Int. Cl.[6] .............................. C12N 9/70; A01N 25/00; A21D 4/00; C11D 17/00
[52] U.S. Cl. ......................... 435/261; 424/405; 426/335; 510/417
[58] Field of Search ............................ 435/261; 424/405; 426/326, 320, 335; 451/903; 210/643; 510/417; 585/514

[56] References Cited

U.S. PATENT DOCUMENTS

| Re. 31,779 | 12/1984 | Alliger | 252/187.23 |
|---|---|---|---|
| 3,719,590 | 3/1973 | Li et al. | 585/818 |
| 3,968,250 | 7/1976 | Boucher | 514/705 |
| 4,941,995 | 7/1990 | Richards | 252/407 |
| 4,943,954 | 7/1990 | Ostlie | 367/191 |
| 5,166,176 | 11/1992 | Obagi et al. | 514/557 |
| 5,482,710 | 1/1996 | Slavtcheff et al. | 424/195.1 |
| 5,503,766 | 4/1996 | Kulperger | 510/383 |

FOREIGN PATENT DOCUMENTS

| 4410778 | 10/1995 | Germany . |
|---|---|---|
| 06133741 | 5/1994 | Japan . |
| 1811852 | 4/1993 | U.S.S.R. . |
| 95/04126 | 2/1995 | WIPO . |

OTHER PUBLICATIONS

Remington's :Pharmaceutical Sciencecs. 18th Edition, Gennaro, Ed. (1990) (Mack Publishing Company: Easton PA), p. 1261.

*Primary Examiner*—Jean C. Witz
*Assistant Examiner*—Susan Hanley
*Attorney, Agent, or Firm*—McHale & Slavin, P.A.

[57] ABSTRACT

The instant invention is a decontaminating process for reducing the surface tension of a biofilm allowing for the removal of the biofilm and control of underlying bacteria. A solution consists of saponin and a soft acid such as food grade sodium lactate. The saponin acts as a foaming agent providing surface tension reduction capable of loosening the biofilm. The solution is preferably applied by a mechanical device providing an efficient coating of the surface to be treated allowing a reduced amount of the lactate acid to be used allowing the acid to make contact with the bacteria while stripping away of the biofilm is made possible.

5 Claims, No Drawings

DECONTAMINATION PROCESS

FIELD OF THE INVENTION

This invention relates to the decontamination of bacteria laden surfaces and in particular to an emulsion formula capable of removing biofilms for proper bacteria destruction.

BACKGROUND OF THE INVENTION

Bacteria is a group of microscopic, unicellular organisms that lack a distinct nucleus and reproduce by cell division. Bacteria typically range from 1 to 10 micrometers and vary in the ways they obtain energy and nourishment. About 200 species of bacteria are pathogenic, pathogenicity varies among the species and is dependent on both the virulence of the species and the condition of the host organism. The *E. coli* 0157:H7 and salmonella microorganisms are just two of the most well known pathogenic bacteria which may cause death in humans.

It is well known that bacteria is involved in the spoilage of food and in particular meat, wine, vegetables, milk and other dairy products. Bacteria may actually render such foods unpalatable by changing their composition. Bacteria growth can also lead to food poisoning such as that caused by clostridium botulinum or staphylococcus aureus. Certain types of bacteria are found in nearly all food products.

Bacteria can be aerobes or anaerobes and are capable of attaching to any surface. Under certain conditions, especially in food processing, bacteria can quickly form a microorganism which seeks a solid surface having nutrients for growth. As the microorganisms grow and multiply, the newly formed cells attach to each other as well as to the surface forming a confluent colony. When the colony becomes sufficiently large, it entraps debris, nutrients, and other microorganisms, wherein a microbial biofilm is established. A biofilm coating enhances the ability of bacteria to resist removal and inactivation. If a biofilm conceals a pathogenic bacteria, the result can lead to illness and death if the bacteria is later introduced to a human.

Common knowledge states that an emphasis must be placed on proper cleaning and sanitizing procedures, especially as those relate to food processing systems. Bacteria that enters a food processing system has an enhanced chance of being consumed by the public. Bacteria are controllable in food processing systems if an effective sanitization program is implemented. For this reason, a myriad of processes are known in the industry all with various levels of effectiveness.

Ozonation, being an allotropic form of oxygen, is used in purifying water, sterilizing air, and treating of foods and the creation of ice. Ozonated ice is commonly used for the storage of fish and chicken carcasses in an attempt to control such bacteria as *Listeria monocytogenes*. However, ozonated ice is only partially effective because of the naturally occurring biofilm that prevents the physical contact of released oxidants with the carcasses during storage. In addition, ozone can create a corrosive environment making it difficult to control.

Irradiation is another known process employed in many parts of the world with limited levels of acceptance and effectiveness. Questions currently remain as to the residual effects of products treated with irradiation and the consuming public. The process is also expensive making it impractical for many applications and limited for use on certain materials. In Europe special labeling requirements are imposed on those foods treated by irradiation with similar measures being considered in the United States.

Various types of acids are used in controlling bacteria, all having various levels of effectiveness. Acids are corrosive, dangerous to handle, and contact with a surface may alter the characteristic of the surface. Acids have limited effectiveness and are not considered effective prior to evisceration because of the nearly impermeable biofilms on the surface of carcasses. In addition, some acids cause taste and color degradation and are not environmentally friendly making disposal of the waste a major consideration. It should be noted that not all acids cause such reactions and those that do not, to any measurable degree, are often referred to as soft acids. However, soft acids are known to be most effective in post evisceration. Lactic acid is currently used in decontamination situations but teachings of the product are limited to destruction of bacteria before a biofilm develops. Once the biofilm develops, the acid is of limited use in spraying or dipping.

Physical removal also remains an option for bacteria control. However, the physical removal of visual contamination by trimming of effected areas, such as on carcasses, creates the risk of spreading the contaminants.

According to industry publications presented by Characklis and Cooksel in 1983 further supplemented by Characklis in 1984, set forth in Food Technology, Article of July 1994, Volume 48, No. 7, the biofilm is considered a five stage process which results from the physical, chemical and biological phenomenon and is identified as follows: transport of nutrients, inorganic, and organic matter to the solid surface; absorption of a conditioning film containing inorganic or organic nutrients; attachment of microbial cells to the wetted surface in initiation of growth; Bacterial metabolism within the biofilm; and cell disruption and detachment from the biofilm.

For these reasons, efforts are constantly under way to discover an economical and safe method for the destruction of bacteria. The problem is that the protective coating made by the biofilm requires treatment strong enough to break through the biofilm, destroy the underlying bacteria, yet not harm or alter the treated product.

What is lacking in the art is a process that is environmentally safe and specifically directed to the removal of the biofilm allowing for subsequent treatment of the underlying bacteria.

SUMMARY OF THE INVENTION

The instant invention is a colloidal emulsion employing saponin within a formulation that, when applied under certain conditions, is capable of reducing the surface tension of a biofilm allowing for removal and control of underlying bacteria. In particular, a triterpene saponin is used which is non-steroidal and commercially available. The saponin operates as a foaming agent, emulsifier, and provides surface tension reduction capable of loosening the biofilm. When the triterpene saponin is placed in a solution and used in conjunction with a soft acid, preferably sodium lactate, the biofilm is removed and the lactate acid kills the bacteria.

Sodium lactate and triterpene saponin when combined can be applied by a mechanical device wherein the emulsion is dispersed at about 1% and 2% respectively by volume of water flowing at a rate of one gallon of water per minute. Because the molecular structure of the triterpene saponin is colloidal, it does not penetrate the surface of the material being treated. In instances where the formulation is used in treating of a carcass, the triterpene saponin will not penetrate the substrate of a carcass, but will penetrate into the substrate.

Triterpene saponin is slightly acidic having a pH of between 4 and 5. It has been observed that a synergism takes place in creating the emulsion by allowing a reduced amount of lactate acid to be used and that a stable, controllable exposure for the acid to contact the bacteria is achieved. At the same time the loosening or stripping away of the biofilm is made possible. In addition, it has been found that increasing the temperature of the solution to over 100° F. further enhances the process.

The formulation is preferably applied by a mechanical device which is calibrated according to the emulsion formula for creating a foam covering the entire surface to be treated. The foam, containing the emulsion, would remain fixed to the surface of the product to be treated for a predescribed period of time then spray rinsed prior to carcass evisceration. When the emulsion is incorporated into a pressurized container or when used by a venturi system, the result is that the emulsion is released in a heavy, natural foam. When applied to a surface, such as a carcass, and remains on the surface between 30 seconds up to an hour, depending upon desired contact time, the foam containing the emulsion begins loosening or stripping away the biofilm. As the biofilm is removed the soft acid is allowed direct contact with the associated bacteria located on the biofilm as well as beneath the biofilm providing exposure time for the destruction of bacteria. Exposure time is critical since the acid requires contact time for effective destruction of bacteria. The amount of contact time required depends upon the type of bacteria that is treated. The emulsion can maintain a firm state for periods in excess of one hour.

Thus, an objective of this invention is to simplify current decontamination processes by teaching an emulsion formulation capable of reducing the surface tension of biofilm for subsequent removal.

Another objective of this invention is to teach a decontamination process that is economical, simple to apply, and environmentally friendly.

Still another objective of the instant invention is to provide a process that requires minimal mechanical adjustments to accommodate numerous existing food processing programs prior to chilling/packaging of a food product.

Yet another objective of the instant invention is to eliminate the need for dip tanks by allowing the necessary contact time for bacterial kill through use of a long lasting emulsion in foam.

Still another objective of the instant invention is to teach a process for use prior to evisceration wherein the run-off provides for maintenance of the underlying cleaning surface.

Other objects and advantages of this invention will become apparent from the following description wherein are set forth, by way of illustration and example, certain embodiments of this invention.

DETAILED DESCRIPTION OF THE PREFERRED EMBODIMENT

Saponins are naturally occurring oily glycosides that foam freely when shaken with water. They occur in a wide variety of plants including acacia, soapwort, soaproot, California pigweed, and many others. The use of a triterpene saponin, commonly referred to as Saponin Departum Levissium Q, is non-steroidal and commercially available. The preferred embodiment of this invention is directed to the triterpene saponin, yet it will be obvious to one of ordinary skill in the art that the various types of saponins may be substituted leading to various levels of success. Unique to the saponin is its ability to operate as a foaming agent and emulsifier leading to surface reduction capabilities. An artificial reproduction of saponin is deemed within the scope of this invention.

Biofilms are known to have a surface tension which acts in a direction parallel to the boundary surface. Water, possessing powerful intermolecular attractive forces, has a high surface tension (72.8 dynes/cm at 20° C.). Many soluble surfaces, mainly organic, when dissolved in water reduce the surface tension even when added in very low concentrations. The inventor has discovered that the incorporation of triterpene saponin, when based on a 5% aqueous solution results in a surface tension of 44.5 dynes/cm.

The instant invention is a colloidal emulsion employing saponin capable of reducing the surface tension of a biofilm allowing for the removal and control of bacteria. The utilization of triterpene saponin having an environmentally safe, non-steroidal make up which operates a foaming agent and emulsifier leading to surface tension reduction that was uncovered to have a unique property capable of loosening the biofilm.

It is recognized that the loosening of or the stripping away of the biofilm in and of itself will not render the product completely bacteria free, therefore a preferred additive to the product would be a soft acid, such as a lactate acid. Sodium lactate is preferred as the USDA allows the use of sodium lactate in meat and poultry products up to 2% of the formulation under 9 CFR 319.180. Sodium lactate 60% food grade is a commercially available lactate acid and can be combined with the saponin at a rate so that when they are applied by a mechanical device the emulsion is dispersed at about 1% and 2% respectively, by volume of water flowing at a rate of one gallon of water per minute. While the above captioned ratio is preferred, it will be obvious to one skilled in the art that a range deviation is possible to meet the conditions of the product and materials used in formulation of the emulsion.

As previously mentioned, the saponin used in the creation of this emulsion are colloidal. The colloidals are thus intermediate between core suspensions on the one hand and molecular or ionic solutions on the other. Because the molecular structure of the triterpene saponin is colloidal, it does not penetrate the surface of the material being treated. In instances where the formulation is used in treating of a carcass, the triterpene saponin penetrates only the substrate of a carcass. The triterpene saponin used in this emulsion has a pH between 4 and 5 and it is noted that a synergism takes place in creating the emulsion by allowing a reduced amount of lactate acid to be used, while at the same time the loosening or stripping away of the biofilm is made possible.

The process employs the formulation through application with a fixed mechanical device which is calibrated according to the emulsion formula creating a foam covering the entire surface to be treated. The foam, containing the emulsion, would remain fixed to the surface of the product to be treated for a predescribed period of time then spray rinsed for removal. In the example of carcasses, after evisceration the process would be repeated prior to chilling. In this manner, the method of decontaminating the entire slaughtering process is minimized and offers an effective solution to the biofilms and related bacteria problem.

When the emulsion is incorporated into a pressurized container the result is that the emulsion is released in a heavy, natural foam which when applied to a surface which can remain on the surface for up to an hour, depending upon desired contact time. The foam which contains the emulsion begins loosening the biofilm permitting the soft acid a direct contact with the associated bacteria located on the biofilm, as well as beneath the biofilm. The exposure time is critical since the ability of any acid requires contact time for effective kill, the actual amount of time depends upon the type of bacteria. In most, if not all cases the amount of exposure time is between 30 seconds and one hour. The Handi-Foam Dispenser, model 297, as sold by the Dema Engineering Company is one known device that operates efficiently with the emulsion.

It is contemplated that any current foaming system can be used in a situation where the process calls for decontamination. In addition, a residual foam continues to suspend the biofilm. For instance, in a slaughtering process, after the carcass is spray rinsed the removed emulsion continues to maintain the micro organisms in a suspended state. The suspended state continues as the solution falls to the processing floor and continues to work in cleaning of the floor or any other surface that the emulsion contacts while the foam is present. This operates to reduce the possibility of cross contamination and allows an entire processing room to be cleaned without the need for testing compatibility of cross decontamination products.

It is noted that the compatibility between the saponin or other foaming agents and acids must fall in a pH range of 4 to 10 when in solution for the emulsion to maintain its foaming properties. This allows a wide variety of foaming agents and cleaning agents to be used. The compatibility of the key substances used in the development of the emulsion can be testing as follows further allowing for the testing of alternatives:

a. Add 300 mm to a laboratory beaker using tap water. It should be noted that the tap water is considered to be potable wherein abnormal levels of chlorine or high dissolved solids will adversely affect the emulsion.

b. Add 5 cc of sodium lactate 60% food grade to the beaker.

c. Add 10 cc of triterpene saponin to the beaker.

d. The solution is shaken until a heavy foam is created which will create a foam approaching the top of the beaker. The beaker can then be unsealed and observed at fifteen minute intervals over a period of one hour. The foam will remain stable with only minor reduction in foam volume nearing the top of the beaker. In this manner, the compatibility of the sodium lactate and the triterpene emulsion is tested for compatibility in a foam state. The same procedure performed without the sodium lactate will provide the same foaming action so as to verify that the soft acid used does not have an adverse affect on the ability of the triterpene saponin to perform.

In the food processing field, another form of bacteria reduction is the use of a dip tank wherein the same tank is used for multiple carcass dipping. The dip tank is notoriously difficult to control as each carcass dip results in bacterial laden material being placed in the tank which will eventually overcome the solution leading to a continuous build up of bacteria. However, the dip tank is required for proper contact time as an acid spray will not adhere to the carcass long enough to provide the required contact time. In this example the instant invention eliminates the need for the dip tank as the emulsion provides the necessary contact time for proper decontamination.

It is to be understood that while a certain form of the invention is illustrated, it is not to be limited to the specific constituents or method of application herein described and shown. It will be apparent to those skilled in the art that various changes may be made without departing from the scope of the invention.

What is claimed is:

1. A process for removal of a biofilm consisting essentially of the steps of:

admixing an effective amount of non-steroidal saponin with an amount of water at about 100 degrees F. to form an emulsion having an effective amount of saponin for removal of a biofilm;

adjusting said emulsion to a pH between 4 and 10;

coating a surface contaminated by a biofilm with said emulsion;

allowing said emulsion to remain on said surface for at least 30 seconds; and removing said emulsion from said surface.

2. The method according to claim 1 wherein said water is maintained at a temperature of about 100 degrees F.

3. The method according to claim 1 wherein said saponin is classified as a triterpene saponin.

4. A process for removal of a biofilm consisting essentially of the steps of:

admixing an effective amount of non-steroidal saponin with an amount of water at about 100 degrees F. to form an emulsion having an effective amount of saponin for removal of a biofilm;

admixing a biocidally effective amount of a solution of sodium lactate to said emulsion, adjusting said emulsion to a pH between 4 and 10;

coating a surface contaminated by a biofilm with said emulsion;

allowing said emulsion to remain on said surface for at least 30 seconds; and removing said emulsion from said surface.

5. The method according to claim 4 wherein said step of admixing a biocidally effective amount of a solution is further defined as admixing an aqueous solution of about 2% saponin and about 1% sodium lactate having a quality suitable for human consumption with water.

* * * * *